(12) United States Patent
Yerkes et al.

(10) Patent No.: US 8,916,498 B2
(45) Date of Patent: *Dec. 23, 2014

(54) SAFENING 6-(TRISUBSTITUTED PHENYL)-4-AMINO-2-PYRIDINECARBOXYLATE HERBICIDE INJURY ON DIRECT SEEDED AND TRANSPLANTED PADDY RICE

(75) Inventors: Carla N. Yerkes, Crawfordsville, IN (US); Paul R. Schmitzer, Indianapolis, IN (US); Richard K. Mann, Franklin, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/620,843

(22) Filed: Nov. 18, 2009

(65) Prior Publication Data

US 2010/0130361 A1  May 27, 2010

Related U.S. Application Data

(60) Provisional application No. 61/117,335, filed on Nov. 24, 2008.

(51) Int. Cl.
*A01N 25/26* (2006.01)
*A01N 25/32* (2006.01)
*A01N 43/40* (2006.01)

(52) U.S. Cl.
CPC ............... *A01N 25/32* (2013.01); *A01N 43/40* (2013.01)
USPC ............................ 504/100; 504/103; 504/105

(58) Field of Classification Search
None
See application file for complete search history.

(56) References Cited

U.S. PATENT DOCUMENTS

| 4,902,340 A | 2/1990 | Hubele |
| 7,314,849 B2 * | 1/2008 | Balko et al. ................... 504/244 |
| 2004/0018940 A1 | 1/2004 | Hacker et al. |

FOREIGN PATENT DOCUMENTS

| WO | WO9418836 A1 | 9/1994 |
| WO | WO2007/082098 A2 | 7/2007 |
| WO | WO-2009/029518 * | 3/2009 |
| WO | WO2009/029518 A2 | 3/2009 |
| WO | WO2010/059671 | 5/2010 |
| WO | WO2010/059676 A2 | 5/2010 |
| WO | WO2010/059680 A2 | 5/2010 |
| WO | WO2010/060581 A2 | 6/2010 |

OTHER PUBLICATIONS

Robinson, Darren K, David W. Monks, and James D. Burton. "Safening Influence of LAB 145 138 on Nicosulfuron, Terbufos and Bentazon Interactions in Sweet Corn (*Zea mays*)." Weed Science, vol. 44, No. 2 (Apr.-Jun. 1996), pp. 339-344.
Kotoula-Syka, Eleni, Kriton K. Hatzios, and Sue A. Meredith. "Interactions between SAN 582H and Selected Safeners on Grain Sorghum (*Sorghum bicolor*) and Corn (*Zea mays*)." Weed Technology, vol. 10, No. 2 (Apr.-Jun. 1996), pp. 299-304.
Hatzios, Kriton K. "Potential safeners for protecting sorghum (*Sorghum bicolor* (L.) Moench) against chlorsulfuron, fluazifop-butyl and sethoxydim." Weed Research, 1984, vol. 24, 249-254.
Frazier, Todd L., Scott J. Nissen. "Influence of Crop Safeners on the Interaction of Primisulfuron and Terbufos in Corn (*Zea mays*)." Weed Science, vol. 42, No. 2 (Apr.-Jun. 1994), pp. 168-171.
International Search Report issued by the EPO, dated Jun. 30, 2011, for International Application No. PCT/US2009/064914, 4 pages.
International Preliminary Report on Patentability, dated Jul. 5, 2011, for International Application No. PCT/US2009/064914, 8 pages.

* cited by examiner

*Primary Examiner* — Alton Pryor
(74) *Attorney, Agent, or Firm* — Michael R. Asam; Michael J. Terapane

(57) ABSTRACT

Herbicidal injury caused by 6-(trisubstituted phenyl)-4-amino-2-pyridinecarboxylates in direct seeded and transplanted paddy rice is reduced with the use of beflubutamid, bispyribac, carfentrazone, cloquintocet, cyhalofop, daimuron, dichlormid, dimepiperate, fenchlorazole, fenclorim, fluxofenim, furilazole, halosulfuron, isoxadifen, mefenpyr, norflurazon, oxabetrinil, pyriclor, sulcotrione, AD67 and mixtures thereof.

16 Claims, No Drawings

SAFENING 6-(TRISUBSTITUTED PHENYL)-4-AMINO-2-PYRIDINECARBOXYLATE HERBICIDE INJURY ON DIRECT SEEDED AND TRANSPLANTED PADDY RICE

This application claims the benefit of U.S. Provisional Application Ser. No. 61/117,335 filed on Nov. 24, 2008. This invention concerns the safening of the herbicidal injury caused by 6-(trisubstituted phenyl)-4-amino-2-pyridinecarboxylates in direct seeded and transplanted paddy rice.

FIELD OF THE INVENTION

Background of the Invention

When agrochemicals, such as plant protection agents and especially herbicides, are used, the cultivated plants may be damaged to a certain degree, depending on factors such as the dose of agrochemicals and their method of application, the species of cultivated plant, the nature of the soil and climatic conditions, for example, length of time of exposure to light, temperature and amounts of precipitation. Thus, it is known that cultivated plants which are to be protected from the adverse effect of undesirable plant growth may be damaged to a certain degree when an effective dose of herbicide is used. Various substances which are capable of specifically preventing the adverse effect of an herbicide on the cultivated plants, i.e. of protecting the cultivated plants without at the same time noticeably influencing the herbicidal action on weeds to be combated, have been proposed to solve this problem. However, it has been found that the antidotes proposed frequently have only a narrow field of use, i.e., a particular antidote is frequently suitable only for use with individual species of cultivated plants and/or for protecting the cultivated plants from individual herbicidal substances or classes of substances.

U.S. Pat. No. 7,314,849 B2 describes certain 6-(polysubstituted aryl)-4-amino-2-pyridinecarboxylate compounds and their use as herbicides. While certain of these compounds have been shown to be particularly effective herbicides for controlling undesirable vegetation in both direct seeded and transplanted paddy rice, they have also been shown to produce slight amounts of damage to the rice at concentrations required to adequately control the undesirable vegetation.

SUMMARY OF THE INVENTION

It has now been found that, surprisingly, the phytotoxic effect of certain 6-(poly-substituted aryl)-4-amino-2-pyridinecarboxylate compounds, which have an auxinic mode of action, on rice can be ameliorated by the use of certain safeners or certain herbicides capable of safening. The present invention concerns a method of protecting direct seeded and transplanted paddy rice from the harmful effects of a 6-(trisubstituted phenyl)-4-amino-2-pyridinecarboxylate herbicide of the formula (I)

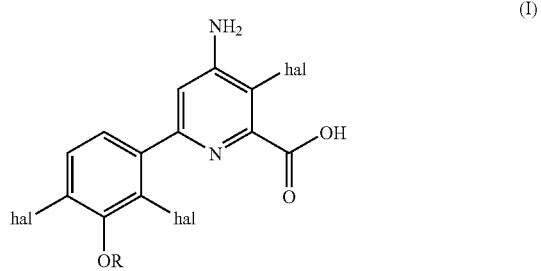

(I)

wherein hal represents F, Cl or Br, and R represents methyl or ethyl,
and its agriculturally acceptable salt, ester and amide derivatives which comprises contacting the direct seeded and transplanted paddy rice with, or applying to the area under cultivation, a safener, or a compatible herbicide capable of safening, selected from the group consisting of AD67, beflubutamid, bispyribac, carfentrazone, cloquintocet, cyhalofop, daimuron, dichlormid, dimepiperate, fenchlorazole, fenclorim, fluxofenim, furilazole, halosulfuron, isoxadifen, mefenpyr, norflurazon, oxabetrinil, pyriclor, sulcotrione, and mixtures thereof.

The present invention also concerns a composition for protecting direct seeded and transplanted paddy rice from the harmful effects of a 6-(trisubstituted phenyl)-4-amino-2-pyridinecarboxylate herbicide of the formula (I)

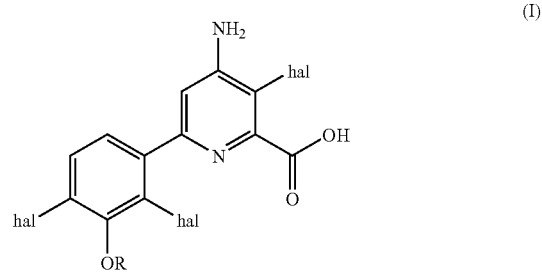

(I)

wherein hal represents F, Cl or Br, and R represents methyl or ethyl,
and its agriculturally acceptable salt, ester and amide derivatives which comprises, in addition to the 6-(trisubstituted phenyl)-4-amino-2-pyridinecarboxylate herbicide, an active safener or compatible herbicide capable of safening selected from the group consisting of AD67, beflubutamid, bispyribac, carfentrazone, cloquintocet, cyhalofop, daimuron, dichlormid, dimepiperate, fenchlorazole, fenclorim, fluxofenim, furilazole, halosulfuron, isoxadifen, mefenpyr, norflurazon, oxabetrinil, pyriclor, sulcotrione, and mixtures thereof. In preferred compositions, the 6-(trisubstituted phenyl)-4-amino-2-pyridinecarboxylate herbicide is a 4-amino-3-chloro-6-(4-chloro-2-fluoro-3-methoxyphenyl)-2-pyridinecarboxylic acid derivative or a 4-amino-3-chloro-6-(2,4-dichloro-3-methoxyphenyl)-2-pyridinecarboxylic acid derivative. In preferred compositions the safener is cloquintocet or isoxadifen.

DETAILED DESCRIPTION OF THE INVENTION

The pyridinecarboxylic acids of formula I are a new class of compounds having herbicidal activity. A number of pyridinecarboxylic acid compounds are described in U.S. Pat. No. 7,314,849 B2, including 4-amino-3-chloro-6-(4-chloro-2-fluoro-3-methoxy-phenyl)pyridine-2-carboxylic acid (compound 1) and 4-amino-3-chloro-6-(2,4-dichloro-3-methoxyphenyl)pyridine-2-carboxylic acid (compound 2). The pyridinecarboxylic acids of formula (I) control annual grass weeds, broadleaf weeds, and sedges in rice, but are also phytotoxic to rice at commercially herbicidal doses.

AD67 (MON 4660) is the common name for 4-(dichloroacetyl)-1-oxa-4-azaspiro-[4,5]decane. Its safening activity is described in *The Pesticide Manual*, Thirteenth Edition, 2003. AD67 (MON 4660) is used as a safener in maize.

Beflubutamid is the common name for 2-[4-fluoro-3-(trifluoromethyl)phenoxy]-N-(phenylmethyl)butanamide. Its herbicidal activity is described in *The Pesticide Manual*, Fourteenth Edition, 2006. Beflubutamid is a compound under development, used either alone or in mixtures with isoproturon, for pre- and early post-emergence control of broadleaf weeds, such as *Veronica persica, Lamium amplexicaule* and *Viola arvensis*, in wheat and barley.

Bispyribac is the common name for 2,6-bis[(4,6-dimethoxy-2-pyrimidinyl)oxy]-benzoic acid. Its herbicidal activity is described in *The Pesticide Manual*, Fourteenth Edition, 2006. Bispyribac-sodium controls grasses, sedges and broadleaf weeds in direct-seeded rice.

Carfentrazone is the common name for α,2-dichloro-5-[4-(difluoromethyl)-4,5-dihydro-3-methyl-5-oxo-1H-1,2,4-triazol-1-yl]-4-fluorobenzenepropanoic acid. Its herbicidal activity is described in *The Pesticide Manual*, Fourteenth Edition, 2006. Carfentrazone-ethyl controls a wide range of broadleaf weeds in cereals and rice.

Cloquintocet is the common name for [5-chloro-8-quinolinyl)oxy]acetic acid. Its safening activity is described in *The Pesticide Manual*, Fourteenth Edition, 2006. Cloquintocet is used as a safener in small grain cereals.

Cyhalofop is the common name for (2R)-2-[4-(4-cyano-2-fluorophenoxy)phenoxy]-propanoic acid. Its herbicidal activity is described in *The Pesticide Manual*, Fourteenth Edition, 2006. Cyhalofop-butyl controls grass weeds in rice.

Daimuron is the common name for N-(4-methylphenyl)-N'-(1-methyl-1-phenylethyl)-urea. Its herbicidal activity is described in *The Pesticide Manual*, Fourteenth Edition, 2006. Daimuron controls cyperaceous and annual grass weeds in paddy rice.

Dichlormid is the common name for N,N-diallyl-2,2-dichloroacetamide. Its safening activity is described in *The Pesticide Manual*, Fourteenth Edition, 2006. Dichlormid is used as a safener for maize and sorghum.

Dimepiperate is the common name for S-(1-methyl-1-phenylethyl) 1-piperidine-carbothioate. Its herbicidal activity is described in *The Pesticide Manual*, Fourteenth Edition, 2006. Dimepiperate controls barnyardgrass (*Echinochloa crusgalli*) in paddy rice.

Fenchlorazole is the common name for 1-(2,4-dichlorophenyl)-5-(trichloromethyl)-1H-1,2,4-triazole-3-carboxylic acid. Its safening activity is described in *The Pesticide Manual*, Fourteenth Edition, 2006. Fenchlorazole is used as a safener in wheat, rye and triticale.

Fenclorim is the common name for 4,6-dichloro-2-phenylpyrimidine. Its safening activity is described in *The Pesticide Manual*, Fourteenth Edition, 2006. Fenclorim is used as a safener in direct-seeded rice.

Fluxofenim is the common name for 1-(4-chlorophenyl)-2,2,2-trifluoroethanone O-(1,3-dioxolan-2-ylmethyl)oxime. Its safening activity is described in *The Pesticide Manual*, Fourteenth Edition, 2006. Fluxofenim is used as a safener in sorghum.

Furilazole is the common name for 3-(dichloroacetyl)-5-(2-furanyl)-2,2-dimethyl-oxazolidine. Its safening activity is described in *The Pesticide Manual*, Fourteenth Edition, 2006. Furilazole is used as a safener in maize.

Halosulfuron is the common name for 3-chloro-5-[[[[(4,6-dimethoxy-2-pyrimidinyl)-amino]carbonyl]amino]sulfonyl]-1-methyl-1H-pyrazole-4-carboxylic acid. Its herbicidal activity is described in *The Pesticide Manual*, Fourteenth Edition, 2006. Halosulfuron-methyl controls annual broadleaf weeds and nutsedge in rice.

Isoxadifen-ethyl is the common name for ethyl 4,5-dihydro-5,5-diphenyl-3-isoxazole-carboxylate. Its safening activity is described in *The Pesticide Manual*, Fourteenth Edition, 2006. Isoxadifen is used as a safener in maize Mefenpyr is the common name for 1-(2,4-dichlorophenyl)-4,5-dihydro-5-methyl-1H-pyrazole-3,5-dicarboxylic acid. Its safening activity is described in *The Pesticide Manual*, Fourteenth Edition, 2006. Mefenpyr is used as a safener in wheat, rye, triticale and barley.

Norflurazon, is the common name for 4-chloro-5-(methylamino)-2-[3-(trifluoro-methyl)phenyl]-3(2H)-pyridazinone. Its herbicidal activity is described in *The Pesticide Manual*, Fourteenth Edition, 2006. Norflurazon is used for the pre-emergence control of grasses and sedges, as well as some broadleaf weeds.

Oxabetrinil is the common name for (αZ)-α-[(1,3-dioxolan-2-yl)methoxyimino]-benzeneacetonitrile. Its safening activity is described in *The Pesticide Manual*, Fourteenth Edition, 2006. Oxabetrinil is used as a safener in sorghum.

Pyriclor is the common name for 2,3,5-trichloro-4-pyridinol.

Sulcotrione is the common name for 2-[2-chloro-4-(methylsulfonyl)benzoyl]-1,3-cyclohexanedione. Its herbicidal activity is described in *The Pesticide Manual*, Fourteenth Edition, 2006. Sulcotrione controls grass and broadleaf weeds.

The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings and established vegetation. The term safener, as used herein, refers to a compound that selectively protects crop plants from herbicide damage without significantly reducing activity in target weed species.

Herbicidal activity is exhibited by the compounds when they are applied directly to the plant or to the locus of the plant via foliar, soil, or water application at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, paddy water quality and depth, and the like, as well as the amount of chemical applied. These and other factors can be adjusted as is known in the art to promote non-selective or selective herbicidal action. Generally, it is preferred to apply the composition of the present invention postemergence to relatively immature undesirable vegetation to achieve the maximum control of weeds.

Cultivated plants which are to be protected from the adverse effect of undesirable plant growth may be damaged to a certain degree when an effective dose of herbicides is used. Safening means preventing the adverse effect of an herbicide on the cultivated plants, i.e., protecting the cultivated plants without, at the same time, noticeably influencing the herbicidal action on weeds to be combated.

In the composition of this invention, the weight ratio of the pyridinecarboxylic acid of formula (I) to the safener at which the herbicidal effect on the cultivated plant is safened lies within the range of between about 2:1 and about 1:32.

The rate at which the safened composition is applied will depend upon the particular type of weed to be controlled, the degree of control required, and the timing and method of application. In general, the composition of the invention can be applied at an application rate of between about 20 grams per hectare (g/ha) and about 1250 g/ha based on the total amount of pyridinecarboxylic acid of formula (I) and safener in the composition. In an especially preferred embodiment of the invention, cloquintocet is applied at a rate between about 13 g/ha and about 560 g/ha and the pyridinecarboxylic acid of formula (I) component is applied at a rate between about 7 g/ha and about 140 g/ha. Also especially preferred is isoxadifen applied at a rate between about 35 g/ha and about 1120 g/ha.

The pyridinecarboxylic acid of formula (I) and the safener of the present invention can be applied either separately or together as part of a multipart herbicidal system.

The herbicide-safener mixture of the present invention can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the rice herbicides that can be employed in conjunction with the safened composition of the present invention include: 2,4-D esters and amines, acetochlor, acifluorfen, aclonifen, AE0172747, alachlor, amidosulfuron, aminocyclopyrachlor, aminotriazole, ammonium thiocyanate, anilifos, atrazine, AVH 301, azimsulfuron, benfuresate, bensulfuron-methyl, bentazone, benthiocarb, benzobicyclon, bifenox, bromacil, bromoxynil, butachlor, butafenacil, butralin, cafenstrole, carbetamide, chlorflurenol, chlorimuron, chlorpropham, cinosulfuron, clethodim, clomazone, clopyralid, cloransulam-methyl, cyclosulfamuron, cycloxydim, dicamba, dichlobenil, dichlorprop-P, diclosulam, diflufenican, diflufenzopyr, dimethenamid, dimethenamid-p, diquat, dithiopyr, diuron, EK2612, EPTC, esprocarb, ET-751, ethoxysulfuron, ethbenzanid, F7967, fenoxaprop, fenoxaprop-ethyl, fenoxaprop-ethyl+ isoxadifen-ethyl, fentrazamide, flazasulfuron, florasulam, fluazifop, fluazifop-P-butyl, flucetosulfuron, flufenacet, flufenpyr-ethyl, flumetsulam, flumiclorac-pentyl, flumioxazin, fluometuron, flupyrsulfuron, fluroxypyr, fomesafen, foramsulfuron, fumiclorac, glufosinate, glufosinate-ammonium, glyphosate, haloxyfop-methyl, haloxyfop-R, imazamethabenz, imazamox, imazapic, imazapyr, imazaquin, imazethapyr, imazosulfuron, indanofan, iodosulfuron, ioxynil, IR 5790, isoproturon, isoxaben, isoxaflutole, KUH-021, lactofen, linuron, MCPA, MCPA ester & amine, mecoprop-P, mefenacet, mesosulfuron, mesotrione, metamifop, metolachlor, metosulam, metribuzin, metsulfuron, molinate, MSMA, napropamide, nicosulfuron, OK-9701, orthosulfamuron, oryzalin, oxadiargyl, oxadiazon, oxazichlomefone, oxyfluorfen, paraquat, pendimethalin, penoxsulam, pentoxazone, pethoxamid, picloram, picolinafen, piperophos, pretilachlor, profoxydim, propachlor, propanil, propyzamide, prosulfocarb, prosulfuron, pyraclonil, pyrazogyl, pyrazosulfuron, pyribenzoxim, pyriftalid, pyriminobac-methyl, primisulfuron, pyroxsulam, quinclorac, quizalofop-ethyl-D, S-3252, sethoxydim, simazine, SL-0401, SL-0402, s-metolachlor, sulfentrazone, sulfosate, tebuthiuron, terbacil, TH-547, thiazopyr, thiobencarb, triclopyr, triclopyr esters and amine, trifluralin and tritosulfuron.

The safened composition of the present invention can, further, be used in conjunction with glyphosate, glufosinate, dicamba, imidazolinones or 2,4-D on glyphosate-tolerant, glufosinate-tolerant, dicamba-tolerant, imidazolinone-tolerant or 2,4-D-tolerant crops. It is generally preferred to use the herbicide-safener mixture of the present invention in combination with herbicides that are selective for the crop being treated and which complement the spectrum of weeds controlled by these compounds at the application rate employed. It is further generally preferred to apply the safened composition of the present invention and other complementary herbicides at the same time, either as a combination formulation or as a tank mix.

In practice, it is preferable to use the safened composition of the present invention in mixtures containing an herbicidally effective amount of the herbicidal components along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art. Some of these adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG (400) dioleate-99.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate;

soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable oils such as soybean oil, rapeseed oil, olive oil, castor oil, sunflower seed oil, coconut oil, corn oil, cotton seed oil, linseed oil, palm oil, peanut oil, safflower oil, sesame oil, tung oil and the like; and esters of the above vegetable oils.

Other additives commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicide-safener mixture of the present invention is generally from 0.001 to 98 percent by weight. Concentrations from 0.01 to 90 percent by weight are often employed. In compositions designed to be employed as concentrates, the active ingredients are generally present in a concentration from 5 to 98 weight percent, preferably 10 to 90 weight percent. Such compositions are typically diluted with an inert carrier, such as water, before application. The diluted compositions usually applied to weeds or the locus of weeds generally contain 0.0001 to 1 weight percent active ingredient and preferably contain 0.001 to 0.05 weight percent.

The present compositions can be applied to weeds or their locus by the use of conventional ground or aerial dusters, sprayers, and granule applicators, by addition to paddy or irrigation water, and by other conventional means known to those skilled in the art.

The following examples illustrate the present invention.
Evaluation of Postemergence Herbicidal Safening in Direct Seeded Rice Seeds or nutlets of the desired test plant species were planted in a soil matrix prepared by mixing a loam soil (43 percent silt, 19 percent clay, and 38 percent sand, with a pH of about 8.1 and an organic matter content of about 1.5 percent) and river sand in an 80 to 20 ratio. The soil matrix was contained in plastic pots with a surface area of 139.7 square centimeters (cm$^2$). When required to ensure good germination and healthy plants, a fungicide treatment and/or other chemical or physical treatment was applied. The plants were grown for 10-17 days (d) in a greenhouse with an approximate 14-hour (h) photoperiod which was maintained at about 29° C. during the day and 26° C. during the night. Nutrients and water were added on a regular basis and supplemental lighting was provided with overhead metal halide 1000-Watt lamps as necessary. The plants were employed for testing when they reached the second or third true leaf stage.

Treatments consisted of esters or salts of compound 1 or compound 2 and various safeners alone and in combination. Weighed amounts were placed in 25 milliliter (mL) glass vials and dissolved in a volume of 97:3 v/v acetone/dimethyl sulfoxide (DMSO) to obtain 12× stock solutions. If the test compound did not dissolve readily, the mixture was warmed and/or sonicated. The concentrated stock solutions were added to the spray solutions so that the final acetone and DMSO concentrations were 16.2% and 0.5%, respectively. Spray solutions were diluted to the appropriate final concentrations with the addition of 10 mL of an aqueous mixture of 1.5% (v/v) Agri-dex crop oil concentrate. The final spray solutions contained 1.25% (v/v) Agri-dex crop oil concentrate. Compound requirements are based upon a 12 mL application volume at a rate of 187 liters/hectare (L/ha). Formulated compounds were applied to the plant material with an overhead Mandel track sprayer equipped with a 8002E nozzle calibrated to deliver 187 L/ha over an application area of 0.503 square meters (m$^2$) at a spray height of 18 inches (43 centimeters (cm)) above average plant canopy height. Control plants were sprayed in the same manner with the solvent blank.

The treated plants and control plants were placed in a greenhouse as described above and watered by sub-irrigation to prevent wash-off of the test compounds. After 3 weeks, the condition of the test plants, compared with that of the untreated plants, was determined visually and scored on a scale of 0 to 100 percent where 0 corresponds to no injury and 100 corresponds to complete kill.

Colby's equation was used to determine the herbicidal effects expected from the mixtures (Colby, S. R. Calculation of the synergistic and antagonistic response of herbicide combinations. *Weeds* 1967, 15, 20-22).

The following equation was used to calculate the expected activity of mixtures containing two active ingredients, A and B:

$$\text{Expected} = A + B - (A \times B/100)$$

A=observed efficacy of active ingredient A at the same concentration as used in the mixture.

B=observed efficacy of active ingredient B at the same concentration as used in the mixture.

Some of the safener-herbicide combinations tested, application rates and ratios employed, plant species tested, and results are given in Tables 1-18.

TABLE 1

Safening Activity of Herbicidal Compositions on Rice

| Application Rate (g ai/ha) | | | Visual Injury (%) | | | | | | | |
|---|---|---|---|---|---|---|---|---|---|---|
| Compound 1 Methyl Ester | Cloquintocet-mexyl | Herbicide: Safener Ratio | 'Lemont' ORYSA | | ECHCO | | SEBEX | | CYPDI | |
| | | | Obs | Exp | Obs | Exp | Obs | Exp | Obs | Exp |
| 35 | 0 | | 45 | | 95 | | 100 | | 100 | |
| 70 | 0 | | 50 | | 99 | | 100 | | 100 | |
| 0 | 35 | | 0 | | 0 | | 0 | | 0 | |
| 0 | 70 | | 0 | | 0 | | 0 | | 0 | |
| 0 | 140 | | 0 | | 0 | | 0 | | 0 | |
| 0 | 280 | | 0 | | 0 | | 0 | | 0 | |

TABLE 1-continued

Safening Activity of Herbicidal Compositions on Rice

| Application Rate (g ai/ha) | | | Visual Injury (%) | | | | | | | |
|---|---|---|---|---|---|---|---|---|---|---|
| Compound 1 Methyl Ester | Cloquintocet-mexyl | Herbicide: Safener Ratio | 'Lemont' ORYSA | | ECHCO | | SEBEX | | CYPDI | |
| | | | Obs | Exp | Obs | Exp | Obs | Exp | Obs | Exp |
| 35 | 35 | 1:1 | 15 | 45 | 95 | 95 | 100 | 100 | 100 | 100 |
| 35 | 70 | 1:2 | 20 | 45 | 90 | 95 | 100 | 100 | 100 | 100 |
| 35 | 140 | 1:4 | 10 | 45 | 90 | 95 | 100 | 100 | 100 | 100 |
| 70 | 70 | 1:1 | 20 | 50 | 95 | 99 | 100 | 100 | 100 | 100 |
| 70 | 140 | 1:2 | 10 | 50 | 95 | 99 | 100 | 100 | 100 | 100 |
| 70 | 280 | 1:4 | 40 | 50 | 95 | 99 | 100 | 100 | 100 | 100 |

TABLE 2

Safening Activity of Herbicidal Compositions on Rice

| Application Rate (g ai/ha) | | | Visual Injury (%) | | | | | | | |
|---|---|---|---|---|---|---|---|---|---|---|
| Compound 1 Methyl Ester | Daimuron | Herbicide: Safener Ratio | 'Lemont' ORYSA | | ECHCO | | SEBEX | | CYPDI | |
| | | | Obs | Exp | Obs | Exp | Obs | Exp | Obs | Exp |
| 35 | 0 | | 45 | | 95 | | 100 | | 100 | |
| 70 | 0 | | 50 | | 99 | | 100 | | 100 | |
| 0 | 35 | | 0 | | 5 | | 0 | | 0 | |
| 0 | 70 | | 0 | | 0 | | 0 | | 0 | |
| 0 | 140 | | 0 | | 0 | | 0 | | 0 | |
| 0 | 280 | | 0 | | 10 | | 0 | | 0 | |
| 35 | 35 | 1:1 | 30 | 45 | 90 | 95 | 100 | 100 | 100 | 100 |
| 35 | 70 | 1:2 | 30 | 45 | 95 | 95 | 100 | 100 | 100 | 100 |
| 35 | 140 | 1:4 | 40 | 45 | 95 | 95 | 100 | 100 | 100 | 100 |
| 70 | 70 | 1:1 | 20 | 50 | 95 | 99 | 100 | 100 | 100 | 100 |
| 70 | 140 | 1:2 | 30 | 50 | 100 | 99 | 100 | 100 | 100 | 100 |
| 70 | 280 | 1:4 | 20 | 50 | 95 | 99 | 100 | 100 | 100 | 100 |

TABLE 3

Safening Activity of Herbicidal Compositions on Rice

| Application Rate (g ai/ha) | | | Visual Injury (%) | | | | | | | |
|---|---|---|---|---|---|---|---|---|---|---|
| Compound 1 Methyl Ester | Fenclorim | Herbicide: Safener Ratio | 'Lemont' ORYSA | | ECHCO | | SEBEX | | CYPDI | |
| | | | Obs | Exp | Obs | Exp | Obs | Exp | Obs | Exp |
| 35 | 0 | | 45 | | 95 | | 100 | | 100 | |
| 70 | 0 | | 50 | | 99 | | 100 | | 100 | |
| 0 | 35 | | 0 | | 0 | | 0 | | 0 | |
| 0 | 70 | | 0 | | 0 | | 0 | | 0 | |
| 0 | 140 | | 0 | | 0 | | 0 | | 0 | |
| 0 | 280 | | 0 | | 0 | | 0 | | 0 | |
| 35 | 35 | 1:1 | 10 | 45 | 95 | 95 | 100 | 100 | 100 | 100 |
| 35 | 70 | 1:2 | 20 | 45 | 95 | 95 | 100 | 100 | 100 | 100 |
| 35 | 140 | 1:4 | 15 | 45 | 95 | 95 | 100 | 100 | 100 | 100 |
| 70 | 70 | 1:1 | 20 | 50 | 95 | 99 | 99 | 100 | 100 | 100 |
| 70 | 140 | 1:2 | 15 | 50 | 95 | 99 | 100 | 100 | 100 | 100 |
| 70 | 280 | 1:4 | 20 | 50 | 95 | 99 | 99 | 100 | 100 | 100 |

TABLE 4

Safening Activity of Herbicidal Compositions on Rice

| Application Rate (g ai/ha) | | | Visual Injury (%) | | | | | | | |
|---|---|---|---|---|---|---|---|---|---|---|
| Compound 1 Methyl Ester | Isoxadifen-ethyl | Herbicide: Safener Ratio | 'Lemont' ORYSA | | ECHCO | | SEBEX | | CYPDI | |
| | | | Obs | Exp | Obs | Exp | Obs | Exp | Obs | Exp |
| 35 | 0 | | 13 | | 100 | | 100 | | 100 | |
| 70 | 0 | | 25 | | 100 | | 100 | | 100 | |

TABLE 4-continued

Safening Activity of Herbicidal Compositions on Rice

| Application Rate (g ai/ha) | | | Visual Injury (%) | | | | | | | |
|---|---|---|---|---|---|---|---|---|---|---|
| Compound 1 Methyl Ester | Isoxadifen-ethyl | Herbicide: Safener Ratio | 'Lemont' ORYSA | | ECHCO | | SEBEX | | CYPDI | |
| | | | Obs | Exp | Obs | Exp | Obs | Exp | Obs | Exp |
| 0 | 17.5 | | 0 | | 0 | | 0 | | 0 | |
| 0 | 35 | | 5 | | 0 | | 0 | | 0 | |
| 0 | 70 | | 10 | | 0 | | 0 | | 0 | |
| 0 | 140 | | 5 | | 0 | | 0 | | 0 | |
| 35 | 17.5 | 2:1 | 5 | 13 | 100 | 100 | 100 | 100 | 100 | 100 |
| 35 | 35 | 1:1 | 0 | 17 | 99 | 100 | 100 | 100 | 100 | 100 |
| 35 | 70 | 1:2 | 15 | 21 | 95 | 100 | 99 | 100 | 100 | 100 |
| 35 | 140 | 1:4 | 5 | 17 | 100 | 100 | 100 | 100 | 100 | 100 |
| 70 | 17.5 | 4:1 | 10 | 25 | 100 | 100 | 100 | 100 | 100 | 100 |
| 70 | 35 | 2:1 | 15 | 29 | 100 | 100 | 100 | 100 | 100 | 100 |
| 70 | 70 | 1:1 | 15 | 33 | 100 | 100 | 100 | 100 | 100 | 100 |
| 70 | 140 | 1:2 | 13 | 29 | 100 | 100 | 100 | 100 | 100 | 100 |

TABLE 5

Safening Activity of Herbicidal Compositions on Rice

| Application Rate (g ai/ha) | | | Visual Injury (%) | | | | | | | |
|---|---|---|---|---|---|---|---|---|---|---|
| Compound 1 Methyl Ester | Oxabetrinil | Herbicide: Safener Ratio | 'Lemont' ORYSA | | ECHCO | | SEBEX | | CYPDI | |
| | | | Obs | Exp | Obs | Exp | Obs | Exp | Obs | Exp |
| 35 | 0 | | 45 | | 95 | | 100 | | 100 | |
| 70 | 0 | | 50 | | 99 | | 100 | | 100 | |
| 0 | 35 | | 0 | | 0 | | 0 | | 0 | |
| 0 | 70 | | 15 | | 0 | | 0 | | 0 | |
| 0 | 140 | | 0 | | 0 | | 0 | | 0 | |
| 0 | 280 | | 10 | | 0 | | 0 | | 0 | |
| 35 | 35 | 1:1 | 20 | 45 | 95 | 95 | 100 | 100 | 100 | 100 |
| 35 | 70 | 1:2 | 15 | 53 | 99 | 95 | 100 | 100 | 100 | 100 |
| 35 | 140 | 1:4 | 30 | 45 | 95 | 95 | 100 | 100 | 100 | 100 |
| 70 | 70 | 1:1 | 15 | 58 | 99 | 99 | 99 | 100 | 100 | 100 |
| 70 | 140 | 1:2 | 40 | 50 | 95 | 99 | 100 | 100 | 100 | 100 |
| 70 | 280 | 1:4 | 20 | 55 | 95 | 99 | 99 | 100 | 100 | 100 |

TABLE 6

Safening Activity of Herbicidal Compositions on Rice

| Application Rate | | | Visual Injury (%) | | | | | | | |
|---|---|---|---|---|---|---|---|---|---|---|
| Compound 1 Methyl Ester (g ae/ha) | Cloquintocet Ester (280 g ae/ha) | Herbicide: Safener Ratio | 'Lemont' ORYSA | | ECHCO | | SEBEX | | CYPDI | |
| | | | Obs | Exp | Obs | Exp | Obs | Exp | Obs | Exp |
| 70 | 0 | | 45 | | 100 | | 100 | | 100 | |
| 35 | 0 | | 35 | | 99 | | 100 | | 100 | |
| 17.5 | 0 | | 15 | | 99 | | 100 | | 100 | |
| 0 | Methyl | | 0 | | 0 | | 0 | | 0 | |
| 70 | Methyl | 1:4 | 35 | 45 | 99 | 100 | 100 | 100 | 100 | 100 |
| 35 | Methyl | 1:8 | 20 | 35 | 100 | 99 | 99 | 100 | 100 | 100 |
| 17.5 | Methyl | 1:16 | 0 | 15 | 95 | 99 | 95 | 100 | 99 | 100 |
| 0 | Ethyl | | 0 | | 0 | | 0 | | 0 | |
| 70 | Ethyl | 1:4 | 25 | 45 | 99 | 100 | 100 | 100 | 100 | 100 |
| 35 | Ethyl | 1:8 | 15 | 35 | 99 | 99 | 99 | 100 | 100 | 100 |
| 17.5 | Ethyl | 1:16 | 10 | 15 | 95 | 99 | 95 | 100 | 100 | 100 |
| 0 | i-Propyl | | 0 | | 0 | | 0 | | 0 | |
| 70 | i-Propyl | 1:4 | 45 | 45 | 99 | 100 | 100 | 100 | 100 | 100 |
| 35 | i-Propyl | 1:8 | 25 | 35 | 99 | 99 | 99 | 100 | 100 | 100 |
| 17.5 | i-Propyl | 1:16 | 10 | 15 | 85 | 99 | 95 | 100 | 100 | 100 |
| 0 | 1-Methylpropyl | | 0 | | 0 | | 0 | | 0 | |
| 70 | 1-Methylpropyl | 1:4 | 15 | 45 | 100 | 100 | 100 | 100 | 100 | 100 |

TABLE 6-continued

Safening Activity of Herbicidal Compositions on Rice

| Application Rate | | | Visual Injury (%) | | | | | | | |
|---|---|---|---|---|---|---|---|---|---|---|
| Compound 1 Methyl Ester (g ae/ha) | Cloquintocet Ester (280 g ae/ha) | Herbicide: Safener Ratio | 'Lemont' ORYSA | | ECHCO | | SEBEX | | CYPDI | |
| | | | Obs | Exp | Obs | Exp | Obs | Exp | Obs | Exp |
| 35 | 1-Methylpropyl | 1:8 | 10 | 35 | 95 | 99 | 100 | 100 | 100 | 100 |
| 17.5 | 1-Methylpropyl | 1:16 | 0 | 15 | 99 | 99 | 95 | 100 | 99 | 100 |
| 0 | Mexyl | | 0 | | 0 | | 0 | | 0 | |
| 70 | Mexyl | 1:4 | 20 | 45 | 100 | 100 | 100 | 100 | 100 | 100 |
| 35 | Mexyl | 1:8 | 10 | 35 | 99 | 99 | 100 | 100 | 100 | 100 |
| 17.5 | Mexyl | 1:16 | 0 | 15 | 95 | 99 | 95 | 100 | 99 | 100 |

TABLE 7

Safening Activity of Herbicidal Compositions on Rice

| Application Rate (g ai/ha) | | | Visual Injury (%) | | | | | | | |
|---|---|---|---|---|---|---|---|---|---|---|
| Compound 1 Na + salt | Cloquintocet-mexyl | Herbicide: Safener Ratio | 'Lemont' ORYSA | | ECHCO | | SEBEX | | CYPDI | |
| | | | Obs | Exp | Obs | Exp | Obs | Exp | Obs | Exp |
| 70 | 0 | | 50 | | 95 | | 100 | | 95 | |
| 0 | 140 | | 0 | | 0 | | 0 | | 0 | |
| 0 | 280 | | 0 | | 0 | | 0 | | 0 | |
| 70 | 140 | 1:2 | 30 | 50 | 95 | 95 | 100 | 100 | 100 | 95 |
| 70 | 280 | 1:4 | 40 | 50 | 90 | 95 | 100 | 100 | 100 | 95 |

TABLE 8

Safening Activity of Herbicidal Compositions on Rice

| Application Rate (g ai/ha) | | | Visual Injury (%) | | | | | | | |
|---|---|---|---|---|---|---|---|---|---|---|
| Compound 1 Na + salt | Fenclorim | Herbicide: Safener Ratio | 'Lemont' ORYSA | | ECHCO | | SEBEX | | CYPDI | |
| | | | Obs | Exp | Obs | Exp | Obs | Exp | Obs | Exp |
| 70 | 0 | | 50 | | 95 | | 100 | | 95 | |
| 0 | 140 | | 0 | | 0 | | 0 | | 0 | |
| 0 | 280 | | 0 | | 0 | | 0 | | 0 | |
| 70 | 140 | 1:2 | 40 | 50 | 95 | 95 | 100 | 100 | 99 | 95 |
| 70 | 280 | 1:4 | 30 | 50 | 95 | 95 | 100 | 100 | 100 | 95 |

TABLE 9

Safening Activity of Herbicidal Compositions on Rice

| Application Rate (g ai/ha) | | | Visual Injury (%) | | | | | | | |
|---|---|---|---|---|---|---|---|---|---|---|
| Compound 2 Na + salt | Cloquintocet-mexyl | Herbicide: Safener Ratio | 'Lemont' ORYSA | | ECHCO | | SEBEX | | CYPDI | |
| | | | Obs | Exp | Obs | Exp | Obs | Exp | Obs | Exp |
| 70 | 0 | | 15 | | 90 | | 100 | | 100 | |
| 0 | 70 | | 0 | | 0 | | 0 | | 0 | |
| 0 | 140 | | 0 | | 0 | | 0 | | 0 | |
| 70 | 70 | 1:1 | 5 | 15 | 90 | 90 | 100 | 100 | 95 | 100 |
| 70 | 140 | 1:2 | 0 | 15 | 90 | 90 | 99 | 100 | 95 | 100 |

TABLE 10

Safening Activity of Herbicidal Compositions on Rice

| Application Rate (g ai/ha) | | | Visual Injury (%) | | | | | | |
|---|---|---|---|---|---|---|---|---|---|
| Compound 2 | | Herbicide: | 'Lemont' ORYSA | | ECHCO | | SEBEX | | CYPDI | |
| Na + salt | Fenclorim | Safener Ratio | Obs | Exp | Obs | Exp | Obs | Exp | Obs | Exp |
| 70 | 0 | | 15 | | 90 | | 100 | | 100 | |
| 0 | 70 | | 0 | | 0 | | 0 | | 0 | |
| 0 | 140 | | 0 | | 0 | | 0 | | 0 | |
| 70 | 70 | 1:1 | 0 | 15 | 90 | 90 | 100 | 100 | 100 | 100 |
| 70 | 140 | 1:2 | 0 | 15 | 95 | 90 | 100 | 100 | 100 | 100 |

TABLE 11

Safening Activity of Herbicidal Compositions on Rice

| Compound 1 | Herbicide: | 'M202' ORYSA Visual Injury (%) | |
|---|---|---|---|
| Methyl Ester | Safener Ratio | Obs | Exp |
| 35 g ai/ha+ | | | |
| No safener | | 35.0 | |
| Cloquintocet-mexyl | 1:16 | 18.3 | 37.2 |
| Daimuron | 1:16 | 26.7 | 37.2 |
| Fenchlorazole-ethyl | 1:16 | 20.0 | 35.0 |
| Furilazole | 1:16 | 23.3 | 37.2 |
| 17.5 g ai/ha+ | | | |
| No safener | | 15.0 | |
| Cloquintocet-mexyl | 1:32 | 3.3 | 17.8 |
| Fenchlorazole-ethyl | 1:32 | 8.3 | 15.0 |
| Fenclorim | 1:32 | 3.3 | 20.7 |
| Fluxofenim | 1:32 | 5.0 | 17.8 |
| Furilazole | 1:32 | 8.3 | 17.8 |
| Mefenpyr-diethyl | 1:32 | 3.3 | 15.0 |

| Safener Alone | Safener Rate g ai/ha | | |
|---|---|---|---|
| Cloquintocet-mexyl | 560 | 3.3 | — |
| Daimuron | 560 | 3.3 | — |
| Fenchlorazole-ethyl | 560 | 0.0 | — |
| Fenclorim | 560 | 6.7 | — |
| Fluxofenim | 560 | 3.3 | — |
| Furilazole | 560 | 3.3 | — |
| Mefenpyr-diethyl | 560 | 0.0 | — |

TABLE 12

Safening Activity of Herbicidal Compositions on Rice

| Compound 1 | Herbicide: | ORYSA Visual Injury (%) | | | | | |
|---|---|---|---|---|---|---|---|
| Methyl Ester | Safener | 'Cheniere' | | 'Cocodrie' | | 'M202' | |
| 17.5 g ai/ha+ | Ratio | Obs | Exp | Obs | Exp | Obs | Exp |
| No safener | | 20 | | 13 | | 45 | |
| Cloquintocet-mexyl | 1:8 | 18 | 20 | 0 | 13 | 27 | 45 |
| Cloquintocet-mexyl | 1:16 | 10 | 20 | 18 | 13 | 27 | 45 |
| Cloquintocet-mexyl | 1:32 | 18 | 20 | 25 | 13 | 25 | 45 |
| Fenchlorazole-ethyl | 1:8 | 8 | 20 | 5 | 13 | 33 | 45 |
| Fenchlorazole-ethyl | 1:16 | 5 | 20 | 5 | 13 | 30 | 45 |
| Fenchlorazole-ethyl | 1:32 | 5 | 20 | 0 | 13 | 25 | 45 |

TABLE 13

Safening Activity of Herbicidal Compositions on Rice

| Compound 1 | Herbicide: | ORYSA Visual Injury (%) | | | | | |
|---|---|---|---|---|---|---|---|
| n-Butyl Ester | Safener | 'Cheniere' | | 'Cocodrie' | | 'M202' | |
| 35 g ai/ha + | Ratio | Obs | Exp | Obs | Exp | Obs | Exp |
| No safener | | 25 | | 20 | | 28 | |
| Cloquintocet-mexyl | 1:2 | 25 | 25 | 25 | 20 | 13 | 28 |
| Cloquintocet-mexyl | 1:4 | 10 | 25 | 20 | 20 | 10 | 28 |
| Cloquintocet-mexyl | 1:8 | 18 | 25 | 3 | 20 | 3 | 28 |
| Fenchlorazole-ethyl | 1:2 | 23 | 25 | 20 | 20 | 13 | 28 |
| Fenchlorazole-ethyl | 1:4 | 18 | 25 | 10 | 20 | 13 | 28 |
| Fenchlorazole-ethyl | 1:8 | 25 | 25 | 5 | 20 | 10 | 28 |

TABLE 14

Safening Activity of Herbicidal Compositions on Rice

| Compound 1 Ester or Salt (g ae/ha) | Cloquintocet-mexyl (g ai/ha) | Herbicide: Safener Ratio | ORYSA Visual Injury (%) | | | | | | | | | | | |
|---|---|---|---|---|---|---|---|---|---|---|---|---|---|---|
| | | | 'Lemont' | | 'Cocodrie' | | 'Cheniere' | | 'M202' | | 'Clearfield' | | 'Wells' | |
| | | | Obs | Exp | Obs | Exp | Obs | Exp | Obs | Exp | Obs | Exp | Obs | Exp |
| Methyl | | | | | | | | | | | | | | |
| 17.5 | 0 | | 40 | | 55 | | 85 | | 25 | | 45 | | 10 | |
| 0 | 140 | | 0 | | 0 | | 0 | | 0 | | 0 | | 0 | |
| 0 | 280 | | 0 | | 0 | | 0 | | 0 | | 0 | | 0 | |
| 17.5 | 140 | 1:8 | 0 | 40 | 10 | 55 | 65 | 85 | 20 | 25 | 25 | 45 | 0 | 10 |
| 17.5 | 280 | 1:16 | 0 | 40 | 0 | 55 | 0 | 85 | 0 | 25 | 0 | 45 | 0 | 10 |
| n-Propyl | | | | | | | | | | | | | | |
| 70 | 0 | | 35 | | 45 | | 45 | | 55 | | 60 | | 15 | |
| 0 | 140 | | 0 | | 0 | | 0 | | 0 | | 0 | | 0 | |
| 0 | 280 | | 0 | | 0 | | 0 | | 0 | | 0 | | 0 | |
| 70 | 140 | 1:2 | 10 | 35 | 60 | 45 | 40 | 45 | 30 | 55 | 50 | 60 | 0 | 15 |
| 70 | 280 | 1:4 | 20 | 35 | 40 | 45 | 30 | 45 | 35 | 55 | 10 | 60 | 0 | 15 |
| Propargyl | | | | | | | | | | | | | | |
| 8.75 | 0 | | 30 | | 35 | | 55 | | 55 | | 50 | | 10 | |
| 0 | 140 | | 0 | | 0 | | 0 | | 0 | | 0 | | 0 | |
| 0 | 280 | | 0 | | 0 | | 0 | | 0 | | 0 | | 0 | |
| 8.75 | 140 | 1:16 | 10 | 30 | 20 | 35 | 60 | 55 | 30 | 55 | 35 | 50 | 10 | 10 |
| 8.75 | 280 | 1:32 | 40 | 30 | 25 | 35 | 40 | 55 | 35 | 55 | 25 | 50 | 15 | 10 |
| Allyl | | | | | | | | | | | | | | |
| 17.5 | 0 | | 25 | | 30 | | 55 | | 55 | | 50 | | 10 | |
| 0 | 140 | | 0 | | 0 | | 0 | | 0 | | 0 | | 0 | |
| 0 | 280 | | 0 | | 0 | | 0 | | 0 | | 0 | | 0 | |
| 17.5 | 140 | 1:8 | 10 | 25 | 40 | 30 | 55 | 55 | 45 | 55 | 35 | 50 | 0 | 10 |
| 17.5 | 280 | 1:16 | 10 | 25 | 55 | 30 | 90 | 55 | 35 | 55 | 40 | 50 | 0 | 10 |
| Et butoxy | | | | | | | | | | | | | | |
| 35 | 0 | | 50 | | 50 | | 50 | | 30 | | 40 | | 15 | |
| 0 | 140 | | 0 | | 0 | | 0 | | 0 | | 0 | | 0 | |
| 0 | 280 | | 0 | | 0 | | 0 | | 0 | | 0 | | 0 | |
| 35 | 140 | 1:4 | 25 | 50 | 30 | 50 | 80 | 50 | 40 | 30 | 40 | 40 | 0 | 15 |
| 35 | 280 | 1:8 | 25 | 50 | 15 | 50 | 35 | 50 | 30 | 30 | 35 | 40 | 0 | 15 |
| K+ Salt | | | | | | | | | | | | | | |
| 8.75 | 0 | | 40 | | 30 | | 50 | | 50 | | 45 | | 0 | |
| 0 | 140 | | 0 | | 0 | | 0 | | 0 | | 0 | | 0 | |
| 0 | 280 | | 0 | | 0 | | 0 | | 0 | | 0 | | 0 | |
| 8.75 | 140 | 1:16 | 20 | 40 | 30 | 30 | 35 | 50 | 20 | 50 | 30 | 45 | 0 | 0 |
| 8.75 | 280 | 1:32 | 0 | 40 | 15 | 30 | 20 | 50 | 20 | 50 | 20 | 45 | 10 | 0 |

TABLE 15

Safening Activity of Herbicidal Compositions on Rice

| Application Rate (g ai/ha) | | ORYSA Visual Injury (%) | | | | | | | |
|---|---|---|---|---|---|---|---|---|---|
| Compound 1 Methyl Ester | Safener | 'Lemont' | | 'Cocodrie' | | 'M202' | | 'Clearfield' | |
| | | Obs | Exp | Obs | Exp | Obs | Exp | Obs | Exp |
| 8.75 | No safener | 10 | | 10 | | 25 | | 30 | |
| 17.5 | No safener | 20 | | 25 | | 30 | | 30 | |
| 35 | No safener | 50 | | 40 | | 40 | | 45 | |
| 70 | No safener | 60 | | 50 | | 55 | | 75 | |
| | Beflubutamid @ 280 | 0 | | 0 | | 10 | | 10 | |
| 8.75 | Beflubutamid @ 280 | 0 | 10 | 0 | 10 | 0 | 33 | 0 | 37 |
| 17.5 | Beflubutamid @ 280 | 0 | 20 | 0 | 25 | 20 | 37 | 10 | 37 |
| 35 | Beflubutamid @ 280 | 10 | 50 | 15 | 40 | 40 | 46 | 20 | 51 |
| 70 | Beflubutamid @ 280 | 10 | 60 | 35 | 50 | 45 | 60 | 30 | 78 |
| | Daimuron @ 140 | 0 | | 20 | | 10 | | 0 | |

TABLE 15-continued

Safening Activity of Herbicidal Compositions on Rice

| Application Rate (g ai/ha) | | ORYSA Visual Injury (%) | | | | | | | |
|---|---|---|---|---|---|---|---|---|---|
| Compound 1 | | 'Lemont' | | 'Cocodrie' | | 'M202' | | 'Clearfield' | |
| Methyl Ester | Safener | Obs | Exp | Obs | Exp | Obs | Exp | Obs | Exp |
| 8.75 | Daimuron @ 140 | 10 | 10 | 0 | 28 | 10 | 33 | 0 | 30 |
| 17.5 | Daimuron @ 140 | 10 | 20 | 0 | 40 | 20 | 37 | 0 | 30 |
| 35 | Daimuron @ 140 | 0 | 50 | 0 | 52 | 35 | 46 | 20 | 45 |
| 70 | Daimuron @ 140 | 45 | 60 | 15 | 60 | 45 | 60 | 35 | 75 |
|  | Fenclorim @ 70 | 0 |  | 0 |  | 0 |  | 0 |  |
| 8.75 | Fenclorim @ 70 | 0 | 10 | 0 | 10 | 0 | 25 | 10 | 30 |
| 17.5 | Fenclorim @ 70 | 0 | 20 | 10 | 25 | 15 | 30 | 20 | 30 |
| 35 | Fenclorim @ 70 | 20 | 50 | 30 | 40 | 20 | 40 | 30 | 45 |
| 70 | Fenclorim @ 70 | 40 | 60 | 30 | 50 | 40 | 55 | 35 | 75 |
|  | Mefenpyr-diethyl @ 140 | 0 |  | 10 |  | 10 |  | 0 |  |
| 8.75 | Mefenpyr-diethyl @ 140 | 20 | 10 | 0 | 19 | 10 | 33 | 0 | 30 |
| 17.5 | Mefenpyr-diethyl @ 140 | 0 | 20 | 10 | 33 | 10 | 37 | 15 | 30 |
| 35 | Mefenpyr-diethyl @ 140 | 15 | 50 | 30 | 46 | 30 | 46 | 35 | 45 |
| 70 | Mefenpyr-diethyl @ 140 | 25 | 60 | 40 | 55 | 35 | 60 | 45 | 75 |

TABLE 16

Safening Activity of Herbicidal Compositions on Rice

| Application Rate (g ai/ha) | | | ORYSA Visual Injury (%) | | | | | | | |
|---|---|---|---|---|---|---|---|---|---|---|
| Compound 1 | | Herbicide: | 'Lemont' | | 'Cocodrie' | | 'M202' | | 'Clearfield' | |
| Methyl Ester | Safener @ 280 | Safener Ratio | Obs | Exp | Obs | Exp | Obs | Exp | Obs | Exp |
| 17.5 | No safener |  | 13 |  | 15 |  | 25 |  | 13 |  |
| 35 | No safener |  | 15 |  | 20 |  | 35 |  | 18 |  |
| 70 | No safener |  | 45 |  | 35 |  | 45 |  | 40 |  |
| 0 | Cloquintocet-methyl |  | 0 |  | 0 |  | 0 |  | 0 |  |
| 17.5 | Cloquintocet-methyl | 1:16 | 0 | 13 | 15 | 15 | 0 | 25 | 0 | 13 |
| 35 | Cloquintocet-methyl | 1:8 | 5 | 15 | 30 | 20 | 25 | 35 | 18 | 18 |
| 70 | Cloquintocet-methyl | 1:4 | 20 | 45 | 15 | 35 | 15 | 45 | 13 | 40 |
| 0 | Cloquintocet-mexyl |  | 0 |  | 0 |  | 10 |  | 0 |  |
| 17.5 | Cloquintocet-mexyl | 1:16 | 0 | 13 | 15 | 15 | 10 | 33 | 18 | 13 |
| 35 | Cloquintocet-mexyl | 1:8 | 15 | 15 | 20 | 20 | 23 | 42 | 13 | 18 |
| 70 | Cloquintocet-mexyl | 1:4 | 28 | 45 | 33 | 35 | 43 | 51 | 30 | 40 |
| 0 | Cloquintocet-mexyl |  | 10 |  | 0 |  | 0 |  | 0 |  |
| 17.5 | Isoxadifen-ethyl | 1:16 | 10 | 21 | 5 | 15 | 5 | 25 | 15 | 13 |
| 35 | Isoxadifen-ethyl | 1:8 | 5 | 24 | 0 | 20 | 5 | 35 | 5 | 18 |
| 70 | Isoxadifen-ethyl | 1:4 | 13 | 51 | 5 | 35 | 15 | 45 | 18 | 40 |

TABLE 17

Safening Activity of Herbicidal Compositions on Rice

| Application Rate (g ai/ha) | | ORYSA Visual Injury (%) | | | | |
|---|---|---|---|---|---|---|
| Compound 1 | | 'Lemont' | | 'Cheniere' | | 'Cocodrie' |
| Methyl Ester | Safener | Obs | Exp | Obs | Exp | Obs | Exp |
| 17.5 | No safener | 20 | | 15 | | 25 | |
| 35 | No safener | 50 | | 40 | | 40 | |
| | Dichlormid @ 140 | 0 | | 0 | | 0 | |
| 17.5 | Dichlormid @ 140 | 10 | 20 | 10 | 15 | 10 | 25 |
| 35 | Dichlormid @ 140 | 20 | 50 | 20 | 40 | 35 | 40 |

TABLE 18

Safening Activity of Herbicidal Compositions on Rice

Application Rate (g ai/ha)

| | | Herbicide: | ORYSA Visual Injury (%) | | | |
|---|---|---|---|---|---|---|
| Compound 1 | | Safener | 'Lemont' | | 'M202' | |
| Methyl Ester | Safener | Ratio | Obs | Exp | Obs | Exp |
| 17.5 | | | 13 | | 25 | |
| 35 | | | 15 | | 35 | |
| 70 | | | 45 | | | |
| 0 | AD67 @ 140 | | 0 | | 0 | |
| 17.5 | AD67 @ 140 | 1:8 | 0 | 13 | 20 | 25 |
| 35 | AD67 @ 140 | 1:4 | 0 | 15 | 20 | 36 |
| 70 | AD67 @ 140 | 1:2 | 40 | 45 | | |
| 0 | AD67 @ 280 | | | | 15 | |
| 17.5 | AD67 @ 280 | 1:16 | | | 15 | 36 |
| 35 | AD67 @ 280 | 1:8 | | | 30 | 45 |
| 0 | Dimepiperate @ 280 | | | | 10 | |
| 17.5 | Dimepiperate @ 280 | 1:16 | | | 15 | 33 |
| 35 | Dimepiperate @ 280 | 1:8 | | | 20 | 42 |
| 0 | Furilazole @ 70 g/ha | | 0 | | | |
| 17.5 | Furilazole @ 70 g/ha | 1:4 | 0 | 13 | | |
| 35 | Furilazole @ 70 g/ha | 1:2 | 0 | 15 | | |
| 70 | Furilazole @ 70 g/ha | 1:1 | 15 | 45 | | |

ORYSA = *Oryza sativa* 'Cheniere,' 'Cocodrie,' 'Lemont,' 'M202,' 'Wells,' and 'Clearfield' (rice)
ECHCO = *Echinochloa colonum* (junglerice)
SEBEX = *Sesbania exaltata* (hemp *sesbania*)
CYPDI = *Cyperus difformis* (small-flower flatsedge)
Obs = observed values
Exp = expected, calculated values
g ai/ha = gram active ingredient per hectare
g ae/ha = gram acid equivalent per hectare Evaluation of Herbicidal Safening in Transplanted Paddy Rice Weed seeds or nutlets of the desired test plant species were planted in puddled soil (mud) prepared by mixing a non-sterilized mineral soil (28 percent silt, 18 percent clay, and 54 percent sand, with a pH of about 7.3 to 7.8 and an organic matter content of about 1.0 percent) and water at a ratio of 100 kilograms (kg) of soil to 19 liters (L) of water. The prepared mud was dispensed in 250 mL aliquots into 480 mL non-perforated plastic pots with a surface area of 91.6 cm$^2$ leaving a headspace of 3 cm in each pot. Rice seeds were planted in Sun Gro MetroMix 306 planting mixture, which typically has a pH of 6.0 to 6.8 and an organic matter content of about 30 percent, in plastic plug trays. Seedlings at the second or third leaf stage of growth were transplanted into 650 mL of mud contained in 960 mL non-perforated plastic pots with a surface area of 91.6 cm$^2$ four days prior to herbicide application. The paddy was created by filling the 3 cm headspace of the pots with water. When required to ensure good germination and healthy plants, a fungicide treatment and/or other chemical or physical treatment was applied. The plants were grown for 4-14 d in a greenhouse with an approximate 14-h photoperiod which was maintained at about 29° C. during the day and 26° C. during the night. Nutrients were added as Osmocote (17:6:10, Nitrogen:Phosphorus:Potassium (N:P:K)+minor nutrients) at 2 grams (g) per cup. Water was added on a regular basis to maintain the paddy flood, and supplemental lighting was provided with overhead metal halide 1000-Watt lamps as necessary. The plants were employed for testing when they reached the second or third true leaf stage.

Treatments consisted of esters and salts of compound 1 or compound 2 and various safeners alone and in combination. For technical grade compounds and safeners, a weighed amount, determined by the highest rate to be tested, was placed in an individual 120 mL glass vial and was dissolved in 20 mL of acetone to obtain concentrated stock solutions. If the test compound did not dissolve readily, the mixture was warmed and/or sonicated. The concentrated stock solutions obtained were diluted with 20 mL of an aqueous mixture containing 2.5% Agri-dex crop oil concentrate (v/v). For formulated compounds and safeners, a weighed amount, determined by the highest rate to be tested, was placed in an individual 120 mL glass vial and was dissolved in 20 mL of 2.5% (v/v) Agri-dex crop oil concentrate to obtain concentrated stock solutions. The concentrated stock solutions obtained were diluted with 20 mL of acetone. Applications were made by injecting an appropriate amount of the stock solution into the aqueous layer of the paddy. Control plants were treated in the same manner with the solvent blank. All treated plant material received the same concentration of acetone and crop oil concentrate.

The treated plants and control plants were placed in a greenhouse as described above and water was added as needed to maintain a paddy flood. After 3 weeks the condition of the test plants, compared with that of the untreated plants, was determined visually and scored on a scale of 0 to 100 percent where 0 corresponds to no injury and 100 corresponds to complete kill.

Some of the compounds tested, application rates employed, plant species tested, and results are given in Tables 19-26.

TABLE 19

Safening Activity of Herbicidal Compositions on Rice

| Application Rate (g ai/ha) | | | Visual Injury (%) | | | | | |
|---|---|---|---|---|---|---|---|---|
| Compound 1 | Cloquintocet- | Herbicide: | 'Lemont' ORYSA | | MOOVA | | CYPDI | |
| Na + salt | mexyl | Safener Ratio | Obs | Exp | Obs | Exp | Obs | Exp |
| 70 | | | 75 | | 100 | | 100 | |
| 0 | 70 | | 0 | | 0 | | 0 | |
| 0 | 140 | | 0 | | 0 | | 0 | |
| 0 | 280 | | 0 | | 0 | | 0 | |
| 70 | 70 | 1:1 | 40 | 75 | 100 | 100 | 100 | 100 |
| 70 | 140 | 1:2 | 35 | 75 | 100 | 100 | 100 | 100 |
| 70 | 280 | 1:4 | 55 | 75 | 100 | 100 | 100 | 100 |

TABLE 20

Safening Activity of Herbicidal Compositions on Rice

| Application Rate (g ai/ha) | | | Visual Injury (%) | | | | | |
|---|---|---|---|---|---|---|---|---|
| Compound 1 | | Herbicide: | 'Lemont' ORYSA | | MOOVA | | CYPDI | |
| Na + salt | Fenclorim | Safener Ratio | Obs | Exp | Obs | Exp | Obs | Exp |
| 70 | | | 75 | | 100 | | 100 | |
| 0 | 70 | | 0 | | 0 | | 0 | |
| 0 | 140 | | 0 | | 0 | | 0 | |
| 0 | 280 | | 0 | | 0 | | 0 | |
| 70 | 70 | 1:1 | 25 | 75 | 100 | 100 | 100 | 100 |
| 70 | 140 | 1:2 | 10 | 75 | 100 | 100 | 100 | 100 |
| 70 | 280 | 1:4 | 25 | 75 | 100 | 100 | 100 | 100 |

TABLE 21

Safening Activity of Herbicidal Compositions on Rice

| Application Rate (g ai/ha) | | | Visual Injury (%) | | | | | |
|---|---|---|---|---|---|---|---|---|
| Compound 2 | Cloquintocet- | Herbicide: | 'Lemont' ORYSA | | MOOVA | | CYPDI | |
| Na + salt | mexyl | Safener Ratio | Obs | Exp | Obs | Exp | Obs | Exp |
| 70 | | | 15 | | 100 | | 100 | |
| 0 | 70 | | 0 | | 0 | | 0 | |
| 0 | 140 | | 0 | | 0 | | 0 | |
| 0 | 280 | | 0 | | 0 | | 0 | |
| 70 | 70 | 1:1 | 0 | 15 | 100 | 100 | 100 | 100 |
| 70 | 140 | 1:2 | 10 | 15 | 100 | 100 | 100 | 100 |
| 70 | 280 | 1:4 | 5 | 15 | 100 | 100 | 100 | 100 |

TABLE 22

Safening Activity of Herbicidal Compositions on Rice

| Application Rate (g ai/ha) | | | Visual Injury (%) | | | | | |
|---|---|---|---|---|---|---|---|---|
| Compound 2 | | Herbicide: | 'Lemont' ORYSA | | MOOVA | | CYPDI | |
| Na + salt | Fenclorim | Safener Ratio | Obs | Exp | Obs | Exp | Obs | Exp |
| 70 | | | 15 | | 100 | | 100 | |
| 0 | 70 | | 0 | | | | | |
| 0 | 140 | | 0 | | 0 | | 0 | |
| 0 | 280 | | 0 | | 0 | | 0 | |
| 70 | 70 | 1:1 | 0 | 15 | 100 | 100 | 100 | 100 |
| 70 | 140 | 1:2 | 0 | 15 | 100 | 100 | 100 | 100 |
| 70 | 280 | 1:4 | 0 | 15 | 100 | 100 | 100 | 100 |

TABLE 23

Safening Activity of Herbicidal Compositions on Rice

| Application Rate (g ae/ha) | | | 'M202' ORYSA Visual Injury (%) | |
|---|---|---|---|---|
| Compound 1 TEA Salt | Cloquintocet-mexyl | Herbicide: Safener Ratio | Obs | Exp |
| 140 | | | 85 | |
| 70 | | | 60 | |
| 0 | 1120 | | 0 | |
| 140 | 1120 | 1:8 | 62 | 85 |
| 70 | 1120 | 1:16 | 35 | 60 |
| 140 | 560 | 1:4 | 67 | 85 |
| 70 | 560 | 1:8 | 25 | 60 |
| 140 | 280 | 1:2 | 77 | 85 |
| 70 | 280 | 1:4 | 30 | 60 |

TABLE 24

Safening Activity of Herbicidal Compositions on Rice

| Application Rate (g ae/ha) | | | 'M202' ORYSA Visual Injury (%) | |
|---|---|---|---|---|
| Compound 1 TEA Salt | Isoxadifen-ethyl | Herbicide: Safener Ratio | Obs | Exp |
| 140 | | | 85 | |
| 70 | | | 60 | |
| 0 | 1120 | | 0 | |
| 140 | 1120 | 1:8 | 8 | 85 |
| 70 | 1120 | 1:16 | 0 | 60 |

TABLE 24-continued

Safening Activity of Herbicidal Compositions on Rice

| Application Rate (g ae/ha) | | | 'M202' ORYSA Visual Injury (%) | |
|---|---|---|---|---|
| Compound 1 TEA Salt | Isoxadifen-ethyl | Herbicide: Safener Ratio | Obs | Exp |
| 140 | 560 | 1:4 | 13 | 85 |
| 70 | 560 | 1:8 | 0 | 60 |
| 140 | 280 | 1:2 | 28 | 85 |
| 70 | 280 | 1:4 | 3 | 60 |

TABLE 25

Safening Activity of Herbicidal Compositions on Rice

| Application Rate (g ae/ha) | | | 'M202' ORYSA Visual Injury (%) | |
|---|---|---|---|---|
| Compound 1 TEA Salt | Mefenpyr-diethyl | Herbicide: Safener Ratio | Obs | Exp |
| 140 | | | 85 | |
| 70 | | | 60 | |
| 0 | 1120 | | 0 | |
| 140 | 1120 | 1:8 | 83 | 85 |
| 70 | 1120 | 1:16 | 45 | 60 |
| 140 | 560 | 1:4 | 65 | 85 |
| 70 | 560 | 1:8 | 33 | 60 |
| 140 | 280 | 1:2 | 63 | 85 |
| 70 | 280 | 1:4 | 40 | 60 |

TABLE 26

Safening Activity of Herbicidal Compositions on Rice

| Application Rate | | | Visual Injury (%) | | | | | |
|---|---|---|---|---|---|---|---|---|
| Compound 1 TEA Salt (g ae/ha) | Isoxadifen-ethyl (g ai/ha) | Herbicide: Safener Ratio | 'M202' ORYSA | | ECHCG | | SCPJU | |
| | | | Obs | Exp | Obs | Exp | Obs | Exp |
| 140 | 0 | | 70 | | 100 | | 100 | |
| 70 | 0 | | 65 | | 99 | | 100 | |
| 0 | 560 | | 0 | | 0 | | 0 | |
| 140 | 560 | 1:4 | 30 | 70 | 100 | 100 | 100 | 100 |
| 70 | 560 | 1:8 | 0 | 65 | 95 | 99 | 100 | 100 |
| 0 | 280 | | 0 | | 0 | | 0 | |
| 140 | 280 | 1:2 | 50 | 70 | 100 | 100 | 100 | 100 |
| 70 | 280 | 1:4 | 15 | 65 | 95 | 99 | 100 | 100 |
| 0 | 140 | | 0 | | 0 | | 0 | |
| 140 | 140 | 1:1 | 55 | 70 | 100 | 100 | 100 | 100 |
| 70 | 140 | 1:2 | 25 | 65 | 100 | 99 | 100 | 100 |

ORYSA = *Oryza sativa* 'Lemont' or 'M202' (rice)
MOOVA = *Monochoria vaginalis* (monochoria)
CYPDI = *Cyperus difformis* (small-flower flatsedge)
ECHCO = *Echinochloa crus-galli* (barnyardgrass)
SCPJU = *Scirpus juncoides* (Japanese bulrush)
TEA = triethylamine
Obs = observed values
Exp = expected, calculated values
g ai/ha = gram active ingredient per hectare
g ae/ha = gram acid equivalent per hectare Evaluation of Postemergence Herbicidal Activity in Direct Seeded Rice Following Rice Seed Treatment Studies were conducted as described in the above "Evaluation of Postemergence Herbicidal Safening in Direct Seeded Rice" section except that rice seeds were soaked for 24 h in 1.9 parts per million (ppm) safener solution prior to direct seeding.

Some of the compounds tested, application rates employed, and results are given in Table 27.

TABLE 27

Safening Activity of Herbicidal Compositions on Rice

| Compound 1 | | | 'Lemont' ORYSA Visual Injury (%) | |
|---|---|---|---|---|
| Formulation | Rate (g ae/ha) | Safener (1.9 ppm) | Obs | Exp |
| Methyl SC | 35 | None | 28.3 | — |
| Methyl SC | 70 | None | 46.7 | — |
| TEA salt SL | 70 | None | 51.7 | — |
| Methyl SC | 35 | Fenchlorazole-ethyl | 15.0 | 28.3 |
| Methyl SC | 70 | Oxabetrinil | 38.3 | 46.7 |
| TEA salt SL | 70 | Fenclorim | 40.0 | 51.7 |

ORYSA = *Oryza sativa* 'Lemont' (rice)
Obs = observed values
Exp = expected, calculated values
g ae/ha = gram acid equivalent per hectare
SC = suspension concentrate
SL = soluble liquid (concentrate)
TEA = triethylamine Evaluation of Herbicidal Activity in Transplanted Paddy Rice Following Seedling Treatment Studies were conducted as described in the above "Evaluation of Herbicidal Safening Transplanted Paddy Rice" except that the roots of rice seedlings at the 1.5 leaf growth stage were soaked in a 1.9 ppm safener solution for 24 h prior to transplanting. Herbicidal compounds were injected into the paddy water immediately following transplanting.

Some of the compounds tested, application rates employed, and results are given in Table 28.

TABLE 28

Safening Activity of Herbicidal Compositions on Rice

| Compound 1 TEA salt | | 'M202' ORYSA Visual Injury (%) | |
|---|---|---|---|
| SL (g ae/ha) | Safener (1.9 ppm) | Obs | Exp |
| 35 | | 45.0 | |
| 70 | | 83.3 | |
| 140 | | 93.3 | |
| 35 | Fenclorim | 30.0 | 45.0 |
| 70 | Fenclorim | 58.3 | 83.3 |
| 140 | Fenclorim | 81.7 | 93.3 |

ORYSA = *Oryza sativa* 'M202' (rice)
Obs = observed values
Exp = expected, calculated values
SL = soluble liquid (concentrate)
TEA = triethylamine
g ae/ha = gram acid equivalent per hectare Evaluation of the Safening Activity of Herbicide Mixtures in Direct Seeded Rice Studies were conducted as described in the above "Evaluation of Postemergence Herbicidal Safening in Direct Seeded Rice" section except that mixtures of known herbicidal compounds provided safening activity on the direct seeded rice crop.

Forms of compound 1 or compound 2 were applied on an acid equivalent (ae) basis. Other herbicidal components were applied on an active ingredient (ai) basis and included acetolactate synthase (ALS)-inhibiting herbicides bispyribac-sodium (pyrimidinylbenzoate chemical class) applied as Regiment 80 DF and halosulfuron-methyl (sulfonylurea chemical class) applied as Permit; protoporphyrinogen IX oxidase (Protox)-inhibiting herbicide carfentrazone-ethyl applied as Aim EC; phytoene desaturase inhibiting herbicide norflurazon; and p-hydroxyphenylpyruvate dioxygenase (HPPD) inhibiting herbicide sulcotrione applied as Mikado.

Some of the compounds tested, application rates employed, and results are given in Tables 29-37. In these tables, g/ha refers to g ae/ha for compounds 1 or 2 and to g ai/ha for the mixing safening partners.

TABLE 29

Safening Activity of Herbicidal Compositions on Rice

| Application Rate (g/ha) | | Visual Injury (%) | |
|---|---|---|---|
| | Bispyribac | 'M202' ORYSA | |
| | sodium | Obs | Exp |
| Compound 1 Methyl Ester | | | |
| 4.38 | 0 | 0 | — |
| 8.75 | 0 | 0 | — |
| 0 | 14 | 25 | — |
| 4.38 | 14 | 0 | 25 |
| 8.75 | 14 | 0 | 25 |
| 8.75 | 0 | 10 | — |
| 17.5 | 0 | 20 | — |
| 0 | 14 | 15 | — |
| 8.75 | 14 | 0 | 24 |
| 17.5 | 14 | 15 | 32 |
| 0 | 28 | 15 | — |
| 8.75 | 28 | 15 | 24 |
| 17.5 | 28 | 15 | 32 |
| Compound 1 n-Butyl Ester | | | |
| 8.75 | 0 | 0 | — |
| 17.5 | 0 | 0 | — |
| 0 | 14 | 25 | — |
| 8.75 | 14 | 0 | 25 |
| 17.5 | 14 | 0 | 25 |
| 35 | 0 | 0 | — |
| 70 | 0 | 0 | — |
| 0 | 14 | 10 | — |
| 35 | 14 | 15 | 15 |
| 70 | 14 | 15 | 24 |
| 0 | 28 | 15 | — |
| 35 | 28 | 10 | 15 |
| 70 | 28 | 0 | 24 |

TABLE 30

Safening Activity of Herbicidal Compositions on Rice

| Application Rate (g/ha) | | ORYSA Visual Injury (%) | | | |
|---|---|---|---|---|---|
| Compound 2 Methyl Ester | Bispyribac sodium | 'M202' | | 'Wells' | |
| | | Obs | Exp | Obs | Exp |
| 8.75 | 0 | 0 | — | 0 | — |
| 17.5 | 0 | 0 | — | 0 | — |
| 0 | 14 | 25 | — | | |
| 8.75 | 14 | 0 | 25 | | |
| 17.5 | 14 | 0 | 25 | | |
| 0 | 28 | 15 | — | 20 | — |

TABLE 30-continued

Safening Activity of Herbicidal Compositions on Rice

| Application Rate (g/ha) | | ORYSA Visual Injury (%) | | | |
|---|---|---|---|---|---|
| Compound 2 Methyl Ester | Bispyribac sodium | 'M202' Obs | Exp | 'Wells' Obs | Exp |
| 8.75 | 28 | 0 | 15 | 0 | 20 |
| 17.5 | 28 | 0 | 15 | 0 | 20 |

TABLE 31

Safening Activity of Herbicidal Compositions on Rice

| Application Rate (g/ha) | | ORYSA Visual Injury (%) | | | |
|---|---|---|---|---|---|
| Compound 1 Methyl Ester | Halosulfuron-methyl | 'M202' Obs | Exp | 'Wells' Obs | Exp |
| 4.38 | 0 | 15 | — | | |
| 8.75 | 0 | 35 | — | | |
| 17.5 | 0 | | | 10 | — |
| 0 | 26 | 0 | — | 10 | — |
| 8.75 | 26 | 20 | 35 | | |
| 17.5 | 26 | | | 0 | 19 |
| 0 | 52 | 15 | — | | |
| 4.38 | 52 | 10 | 28 | | |
| 8.75 | 52 | 30 | 45 | | |

TABLE 32

Safening Activity of Herbicidal Compositions on Rice

| Application Rate (g/ha) | | Visual Injury (%) | |
|---|---|---|---|
| | Halosulfuron-methyl | 'M202' ORYSA Obs | Exp |
| Compound 1 n-Butyl Ester | | | |
| 8.75 | 0 | 0 | — |
| 17.5 | 0 | 10 | — |
| 0 | 26 | 0 | — |
| 17.5 | 26 | 0 | 10 |
| 0 | 52 | 15 | — |
| 8.75 | 52 | 0 | 15 |
| 17.5 | 52 | 0 | 24 |
| Compound 2 Methyl Ester | | | |
| 8.75 | 0 | 0 | — |
| 17.5 | 0 | 0 | — |
| 0 | 52 | 15 | — |
| 8.75 | 52 | 0 | 15 |
| 17.5 | 52 | 0 | 15 |

TABLE 33

Safening Activity of Herbicidal Compositions on Rice

| Application Rate (g/ha) | | ORYSA Visual Injury (%) | | | |
|---|---|---|---|---|---|
| Compound 1 Methyl Ester | Carfentrazone-ethyl | 'M202' Obs | Exp | 'Wells' Obs | Exp |
| 4.38 | 0 | 15 | — | 0 | — |
| 8.75 | 0 | 10 | — | 0 | — |
| 0 | 56 | 20 | — | 25 | — |
| 4.38 | 56 | 10 | 32 | 5 | 25 |
| 8.75 | 56 | 10 | 28 | 5 | 25 |
| 0 | 112 | 20 | — | 35 | — |
| 4.38 | 112 | 10 | 32 | 15 | 35 |
| 8.75 | 112 | 15 | 28 | 20 | 35 |

TABLE 34

Safening Activity of Herbicidal Compositions on Rice

| Application Rate (g/ha) | | ORYSA Visual Injury (%) | | | |
|---|---|---|---|---|---|
| Compound 1 n-Butyl Ester | Carfentrazone-ethyl | 'M202' Obs | Exp | 'Wells' Obs | Exp |
| 8.75 | 0 | 0 | — | 0 | — |
| 17.5 | 0 | 0 | — | 0 | — |
| 0 | 56 | 20 | — | 25 | — |
| 8.75 | 56 | 15 | 20 | 5 | 25 |
| 17.5 | 56 | 15 | 20 | 15 | 25 |
| 0 | 112 | 20 | — | 35 | — |
| 8.75 | 112 | | | 20 | 35 |
| 17.5 | 112 | 15 | 20 | 15 | 35 |

TABLE 35

Safening Activity of Herbicidal Compositions on Rice

| Application Rate (g/ha) | | ORYSA Visual Injury (%) | | | |
|---|---|---|---|---|---|
| Compound 2 Methyl Ester | Carfentrazone-ethyl | 'M202' Obs | Exp | 'Wells' Obs | Exp |
| 8.75 | 0 | 0 | — | 0 | — |
| 17.5 | 0 | 0 | — | 0 | — |
| 0 | 56 | 20 | — | 25 | — |
| 8.75 | 56 | 10 | 20 | 10 | 25 |
| 17.5 | 56 | 15 | 20 | 5 | 25 |
| 0 | 112 | 20 | — | 35 | — |
| 8.75 | 112 | 10 | 20 | | |
| 17.5 | 112 | 15 | 20 | 10 | 35 |

TABLE 36

Safening Activity of Herbicidal Compositions on Rice

| Application Rate (g/ha) | | Visual Injury (%) | |
|---|---|---|---|
| Compound 1 Allyl Ester | Norflurazon | 'M202' ORYSA Obs | Exp |
| 8.75 | 0 | 10 | — |
| 17.5 | 0 | 20 | — |
| 0 | 70 | 15 | — |
| 8.75 | 70 | 10 | 24 |
| 17.5 | 70 | 20 | 32 |

TABLE 37

Safening Activity of Herbicidal Compositions on Rice

| Application Rate (g/ha) | | Visual Injury (%) 'Wells' ORYSA | |
|---|---|---|---|
| | Sulcotrione | Obs | Exp |
| Compound 1 Methyl Ester | | | |
| 4.38 | 0 | 0 | — |
| 8.75 | 0 | 0 | — |
| 0 | 280 | 99 | — |
| 4.38 | 280 | 80 | 99 |
| 8.75 | 280 | 20 | 99 |
| Compound 1 Allyl Ester | | | |
| 17.5 | 0 | 0 | — |
| 35 | 0 | 0 | — |
| 0 | 280 | 99 | — |
| 17.5 | 280 | 20 | 99 |
| 35 | 280 | 40 | 99 |

ORYSA = *Oryza sativa* 'M202' or 'Wells' (rice)
Obs = observed values
Exp = expected, calculated values Evaluation of the Safening Activity of Herbicide Mixtures in Transplanted Paddy Rice Studies were conducted as described in the above "Evaluation of Postemergence Herbicidal Safening in Transplanted Paddy Rice" section except that mixtures of known herbicidal compounds provided safening activity on the transplanted paddy rice crop.

Forms of compound 1 were applied on an acid equivalent basis. Other herbicidal components were applied on an active ingredient bases and included an acetyl CoA carboxylase (ACCase) inhibiting herbicide cyhalofop-butyl applied as Clincher G; p-hydroxyphenylpyruvate dioxygenase (HPPD) inhibiting herbicide sulcotrione applied as Mikado; and another carotenoid biosynthesis inhibitor pyriclor.

Some of the compounds tested, application rates employed, and results are given in Tables 38-40. In these tables, g/ha refers to g ae/ha for compounds 1 or 2 and to g ai/ha for the mixing safening partners.

TABLE 38

Safening Activity of Herbicidal Compositions on Rice

| Application Rate (g/ha) | | Visual Injury (%) 'M202' ORYSA | |
|---|---|---|---|
| Compound 1 TEA Salt | Cyhalofop-butyl | Obs | Exp |
| 70 | 0 | 35 | — |
| 0 | 90 | 0 | — |
| 70 | 90 | 10 | 35 |
| 0 | 180 | 0 | — |
| 70 | 180 | 10 | 35 |

TABLE 39

Safening Activity of Herbicidal Compositions on Rice

| Application Rate (g/ha) | | Visual Injury (%) 'M202' ORYSA | |
|---|---|---|---|
| | Sulcotrione | Obs | Exp |
| Compound 1 Methyl Ester | | | |
| 35 | 0 | 0 | — |
| 70 | 0 | 20 | — |
| 0 | 280 | 10 | — |
| 35 | 280 | 0 | 10 |
| 70 | 280 | 20 | 28 |
| Compound 1 TEA Salt | | | |
| 35 | 0 | 20 | — |
| 70 | 0 | 50 | — |
| 0 | 280 | 10 | — |
| 35 | 280 | 20 | 28 |
| 70 | 280 | 30 | 55 |

TABLE 40

Safening Activity of Herbicidal Compositions on Rice

| Application Rate (g/ha) | | Visual Injury (%) 'M202' ORYSA | |
|---|---|---|---|
| | Pyriclor | Obs | Exp |
| Compound 1 Methyl Ester | | | |
| 70 | 0 | 20 | — |
| 0 | 140 | 0 | — |
| 70 | 140 | 10 | 20 |
| Compound 1 TEA Salt | | | |
| 70 | 0 | 50 | — |
| 0 | 140 | 0 | — |
| 70 | 140 | 25 | 50 |

ORYSA = *Oryza sativa* 'M202' or 'Wells' (rice)
Obs = observed values
Exp = expected, calculated values

What is claimed is:

1. A composition for protecting direct seeded and transplanted paddy rice from the harmful effects of a 6-(trisubstituted phenyl)-4-amino-2-pyridinecarboxylate herbicide of the formula (I)

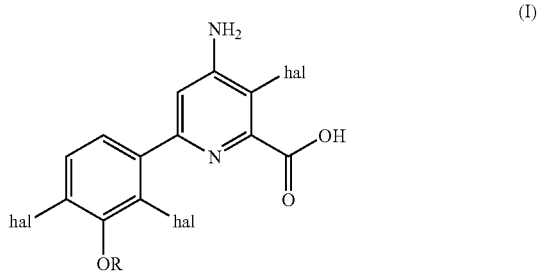

wherein hal represents F, Cl or Br, and R represents methyl or ethyl,
and its agriculturally acceptable salt, ester and amide derivatives which comprises, in addition to the 6-(trisubstituted phenyl)-4-amino-2-pyridinecarboxylate herbicide, an active safener or compatible herbicide capable of safening, selected from the group consisting of: bispyribac, cyhalofop, halosulfuron, norflurazon, pyriclor, sulcotrione, and mixtures thereof, and wherein the weight ratio of the 6-(trisubstituted phenyl)-4-amino-2-pyridinecarboxylate herbicide to the safener is from about 1:1 to about 1:32; wherein the composition comprising the herbicide of formula (I) and the active safener or the compatible herbicide capable of safening is more effective at reducing injury to rice than a composition comprising the herbicide of formula (I) without the active safener or the compatible herbicide capable of safening being present or a composition comprising the active safener or the compatible herbicide capable of safening without the herbicide of formula (I) being present.

2. The composition of claim 1 in which the 6-(trisubstituted phenyl)-4-amino-2-pyridinecarboxylate herbicide is a 4-amino-3-chloro-6-(4-chloro-2-fluoro-3-methoxyphenyl)-2-pyridinecarboxylic acid derivative or a 4-amino-3-chloro-6-(2,4-dichloro-3-methoxyphenyl)-2-pyridinecarboxylic acid derivative.

3. The composition of claim 1 in which the weight ratio of the 6-(trisubstituted phenyl)-4-amino-2-pyridinecarboxylate herbicide to the safener is between about 1:8 and about 1:32.

4. The composition according to claim 1, where the active safener or compatible herbicide capable of safening is bispyribac and wherein the weight ratio of the 6-(trisubstituted phenyl)-4-amino-2-pyridinecarboxylate herbicide to the safener is from about 1:1 to about 1:3.2.

5. The composition according to claim 1, where the active safener or compatible herbicide capable of safening is cyhalofop and wherein the weight ratio of the 6-(trisubstituted phenyl)-4-amino-2-pyridinecarboxylate herbicide to the safener is from about 1:1.3 to about 1:2.57.

6. The composition according to claim 1, where the active safener or compatible herbicide capable of safening is halosulfuron and wherein the weight ratio of the 6-(trisubstituted phenyl)-4-amino-2-pyridinecarboxylate herbicide to the safener is from about 1:1.5 to about 1:12.

7. The composition according to claim 1, where the active safener or compatible herbicide capable of safening is norflurazon and wherein the weight ratio of the 6-(trisubstituted phenyl)-4-amino-2-pyridinecarboxylate herbicide to the safener is from about 1:4 to about 1:8.

8. The composition according to claim 1, where the active safener or compatible herbicide capable of safening is pyriclor and wherein the weight ratio of the 6-(trisubstituted phenyl)-4-amino-2-pyridinecarboxylate herbicide to the safener is about 1:2.

9. The composition according to claim 1, where the active safener or compatible herbicide capable of safening is sulcotrione and wherein the weight ratio of the 6-(trisubstituted phenyl)-4-amino-2-pyridinecarboxylate herbicide to the safener is from about 1:4 to about 1:8.

10. A method of protecting direct seeded and transplanted paddy rice from the harmful effects of a 6-(trisubstituted phenyl)-4-amino-2-pyridinecarboxylate herbicide of the formula (I)

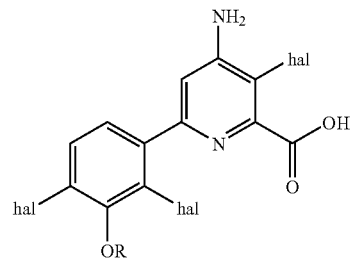

wherein hal represents F, Cl or Br, and R represents methyl or ethyl, and its agriculturally acceptable salt, ester and amide derivatives which comprises contacting the direct seeded or transplanted paddy rice with, or applying to the area under cultivation of direct seeded or transplanted paddy rice, a safener, or a compatible herbicide capable of safening, selected from the group consisting of: bispyribac, cyhalofop, halosulfuron, norflurazon, pyriclor, sulcotrione, and mixtures thereof, and wherein the weight ratio of the 6-(trisubstituted phenyl)-4-amino-2-pyridinecarboxylate herbicide to the safener is from about 1:1 to about 1:32; wherein the composition comprising the herbicide of formula (I) and the active safener or the compatible herbicide capable of safening is more effective at reducing injury to rice than a composition comprising the herbicide of formula (I) without the active safener or the compatible herbicide capable of safening being present or a composition comprising the active safener or the compatible herbicide capable of safening without the herbicide of formula (I) being present.

11. The method according to claim 7, where the active safener or compatible herbicide capable of safening is bispyribac and wherein the weight ratio of the 6-(trisubstituted phenyl)-4-amino-2-pyridinecarboxylate herbicide to the safener is from about 1:1 to about 1:3.2.

12. The method according to claim 7, where the active safener or compatible herbicide capable of safening is cyhalofop and wherein the weight ratio of the 6-(trisubstituted phenyl)-4-amino-2-pyridinecarboxylate herbicide to the safener is from about 1:1.3 to about 1:2.57.

13. The method according to claim 7, where the active safener or compatible herbicide capable of safening is halosulfuron and wherein the weight ratio of the 6-(trisubstituted phenyl)-4-amino-2-pyridinecarboxylate herbicide to the safener is from about 1:1.5 to about 1:12.

14. The method according to claim 7, where the active safener or compatible herbicide capable of safening is norflurazon and wherein the weight ratio of the 6-(trisubstituted phenyl)-4-amino-2-pyridinecarboxylate herbicide to the safener is from about 1:4 to about 1:8.

15. The method according to claim 7, where the active safener or compatible herbicide capable of safening is pyriclor and wherein the weight ratio of the 6-(trisubstituted phenyl)-4-amino-2-pyridinecarboxylate herbicide to the safener is about 1:2.

16. The method according to claim 7, where the active safener or compatible herbicide capable of safening is sulcotrione and wherein the weight ratio of the 6-(trisubstituted phenyl)-4-amino-2-pyridinecarboxylate herbicide to the safener is from about 1:4 to about 1:8.

* * * * *